US008821372B2

(12) United States Patent
von Pechmann et al.

(10) Patent No.: US 8,821,372 B2
(45) Date of Patent: Sep. 2, 2014

(54) ENDOSCOPIC MESH DELIVERY SYSTEM WITH INTEGRAL MESH STABILIZER AND VAGINAL PROBE

(76) Inventors: Walter von Pechmann, Bethesda, MD (US); Samuel C. Yoon, Clarksville, MD (US); Keith Lipford, Baltimore, MD (US); Brian Lipford, Bel Air, MD (US); Austin Cox, Silver Spring, MD (US)

( * ) Notice: Subject to any disclaimer, the term of this patent is extended or adjusted under 35 U.S.C. 154(b) by 303 days.

(21) Appl. No.: 12/973,189

(22) Filed: Dec. 20, 2010

(65) Prior Publication Data

US 2011/0174313 A1    Jul. 21, 2011

Related U.S. Application Data

(63) Continuation-in-part of application No. 12/746,658, filed as application No. PCT/US2008/013661 on Dec. 12, 2008.

(60) Provisional application No. 61/284,457, filed on Dec. 18, 2009.

(51) Int. Cl.
*A61F 2/00* (2006.01)
*A61F 13/00* (2006.01)
*A61B 17/08* (2006.01)
*A61B 17/42* (2006.01)
*A61B 17/00* (2006.01)

(52) U.S. Cl.
CPC ....... *A61B 17/42* (2013.01); *A61B 2017/00876* (2013.01); *A61B 17/00234* (2013.01); *A61F 2/0045* (2013.01)
USPC ................................ 600/37; 600/30; 606/151

(58) Field of Classification Search
USPC .............. 600/30, 37, 450, 462, 591; 606/139, 606/151; 623/23.72; 604/515; 128/834, 838
See application file for complete search history.

(56) References Cited

U.S. PATENT DOCUMENTS

| 3,786,807 | A | * | 1/1974 | Dubin ........................... 128/838 |
| 6,143,005 | A | * | 11/2000 | Yoon et al. .................... 606/148 |
| 6,328,729 | B1 | | 12/2001 | Jervis |
| 6,741,895 | B1 | | 5/2004 | Gafni et al. |
| 6,932,759 | B2 | | 8/2005 | Kammerer et al. |
| 7,052,453 | B2 | | 5/2006 | Presthus et al. |

(Continued)

OTHER PUBLICATIONS

Culligan et al., Long-term success of abdominal sacral colpopexy using synthetic mesh, Am. J. Obstet Gynecol, Dec. 2002.

*Primary Examiner* — Jacqueline Cheng
*Assistant Examiner* — Eileen Foley
(74) *Attorney, Agent, or Firm* — Ober, Kaler, Grimes & Shriver; Royal W. Craig

(57) ABSTRACT

A mesh delivery system for sacral colpopexy procedures is disclosed. The system uses a mesh stabilizer (30) that is introduced in a compressed configuration through a surgical port into the abdomen, and a vaginal probe (10) (inserted through the vagina) with a magnetic or non-magnetic head that engages with the mesh stabilizer (30), anchoring it in position. The mesh stabilizer (30) employs a pseudoelastic shape memory alloy, and folds compact to deliver multiple mesh straps or a single Y-shaped surgical mesh in a streamlined configuration into the abdomen for facilitating the sacral colpopexy procedure. After delivery, the stabilizer (30) expands to a functional configuration where it interfaces with the probe (10) head and stabilizes and adjustably feeds the mesh strap(s) for suturing while maintaining stabilization of the mesh on the vaginal apex and while keeping excess mesh from obscuring the surgeons view. After suturing, the stabilizer can be removed back through the surgical port.

22 Claims, 6 Drawing Sheets

(56) References Cited

U.S. PATENT DOCUMENTS

| | | |
|---|---|---|
| 2003/0195386 A1 | 10/2003 | Thierfelder et al. |
| 2003/0220538 A1 | 11/2003 | Jacquetin |
| 2005/0245787 A1* | 11/2005 | Cox et al. .................. 600/37 |
| 2006/0015001 A1 | 1/2006 | Staskin et al. |
| 2006/0199994 A1 | 9/2006 | Inman et al. |
| 2007/0129615 A1* | 6/2007 | Backman et al. ............ 600/315 |
| 2007/0156012 A1* | 7/2007 | Tracey et al. ................. 600/30 |
| 2008/0119891 A1* | 5/2008 | Miles et al. .................. 606/213 |
| 2008/0188874 A1* | 8/2008 | Henderson .................. 606/151 |
| 2009/0254103 A1* | 10/2009 | Deutsch ....................... 606/151 |
| 2010/0010501 A2* | 1/2010 | Meade et al. ................ 606/119 |
| 2011/0015477 A1* | 1/2011 | Montpetit et al. ............. 600/37 |

* cited by examiner

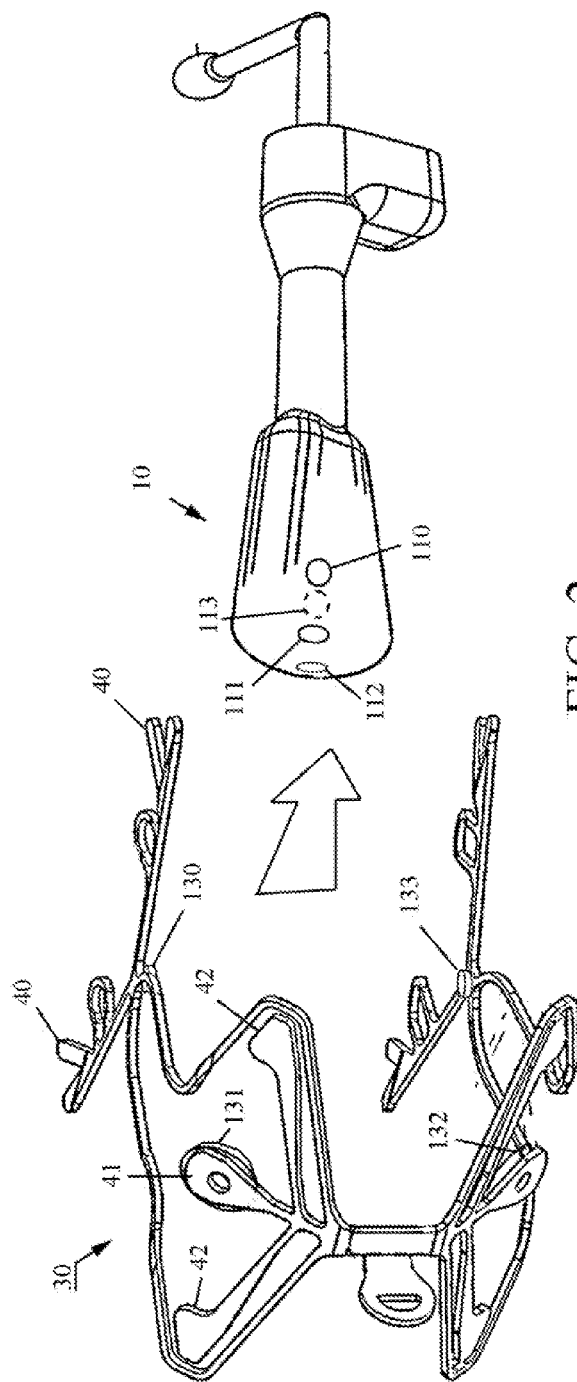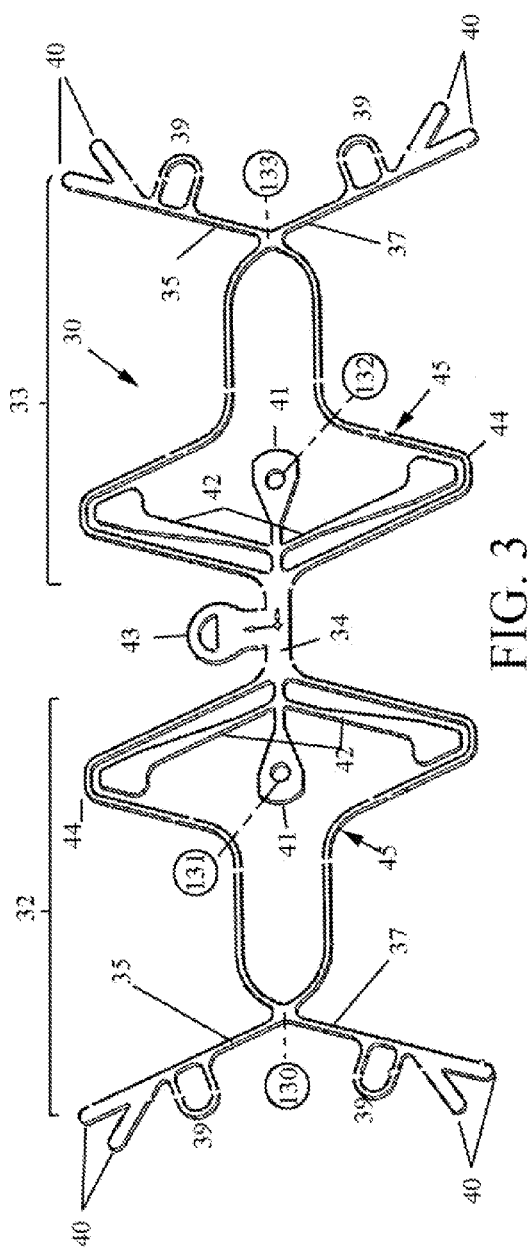
FIG. 2
FIG. 3

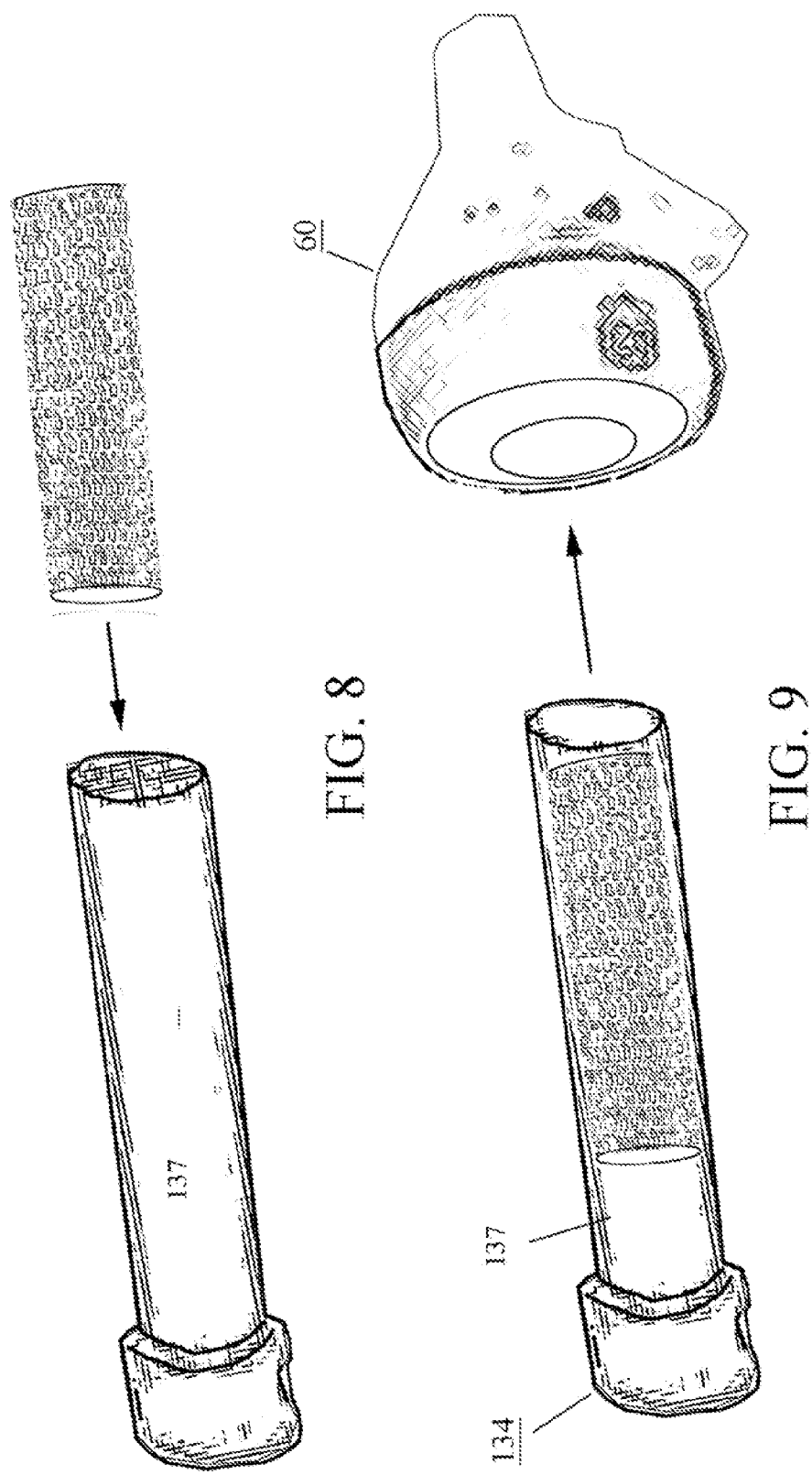

ENDOSCOPIC MESH DELIVERY SYSTEM WITH INTEGRAL MESH STABILIZER AND VAGINAL PROBE

CROSS-REFERENCE TO RELATED APPLICATIONS

The present application derives priority from U.S. provisional application Ser. No. 61/284,457 filed 18 Dec. 2009, and is a continuation-in-part of U.S. Ser. No. 12/746,658 filed on Jun. 7, 2010, which is a National Stage Entry of PCT/US08/13661 filed Dec. 12, 2008.

BACKGROUND OF THE INVENTION

1. Field of the Invention

The present invention relates to medical methods and devices for performing sacral colpopexy.

2. Background Art

The sacral colpopexy operation is designed to recreate support to the upper vagina by attaching straps of permanent synthetic mesh to the upper anterior and posterior vaginal walls and then suspending the other end of the straps on the anterior surface of the sacrum. This operation is one of many operations described for the correction of pelvic organ prolapse but is considered the gold standard for correction of prolapse of the upper vagina. See, for example, "Long-Term Success of Abdominal Sacral Colpopexy Using Synthetic Mesh", Culligan et al. Am J Obstet Gynecol (December 2002). This operation can be done either for correction of vaginal vault prolapse in patients who have previously undergone hysterectomy or can be done at the time of hysterectomy in patients with uterine prolapse. In the latter case, many physicians prefer to perform supracervical hysterectomy because of data suggesting that mesh related complications are less likely in cases of supracervical compared with total hysterectomy.

The sacral colpopexy operation was first described as being done through a large incision in the abdominal wall (laparotomy) and is still predominantly done in that manner.

FIG. 1 is a diagrammatic illustration of the surgery, which is usually performed under general anesthesia. An incision is made in the lower abdomen. The bladder and rectum are freed from the vagina and permanent mesh is secured to the sacrum (upper tailbone) to support the front and back wall of the vagina. The mesh is sutured to the vagina. The peritoneum (lining of the abdominal cavity) is closed over the mesh. There is growing interest in performing this operation via less invasive approaches, such as laparoscopy or robot-assisted laparoscopic surgery, but existing vaginal probes, surgical instruments and mesh configurations are not well-suited for this.

There are a variety of vaginal probes and mesh configurations designed for use in treating disorders of the female pelvic floor such as pelvic organ prolapse, urinary incontinence, and sexual dysfunction.

For example, U.S. Pat. No. 6,741,895 to Gafni et al. (Medoc Ltd.) issued May 25, 2004 shows a vaginal probe and method for stimulation of the nerves of the vagina with the purpose of testing their reaction to stimuli in the hope of defining, and treating sexual dysfunction in women. A balloon structure is used to provide tactile stimuli. When the balloon is inflated, these projections poke into the vagina.

United States Patent Application 20060199994 by Inman et al. (AMS Research) issued Sep. 7, 2006 shows surgical instruments useful in pelvic floor repair procedures. The claims require a handle attached to a slender, metal, curved rod.

United States Patent Application 20030220538 to Jacquetin issued 27 Nov. 2003 discloses a particular mesh implant for treating anterior vaginal prolapse.

U.S. Pat. No. 6,932,759 to Kammerer et al. issued Aug. 23, 2005 shows a surgical instrument and method for treating female urinary incontinence with a curved needle-like element and a proximal tape, or mesh, for implanting into the lower abdomen of a female to provide support to the urethra. A second curved needle element is used for simultaneous attachment to the distal end of the first needle.

The IVS Tunneller™ device is available from U.S. Surgical of Norwalk, Conn. The IVS device comprises a fixed delta wing handle, a hollow metal tube and a stylet that is placeable within the tube. The stylet has a rounded plastic tip on one end and an eyelet at the other end. The device may be used to implant a polypropylene tape for infracoccygeal sacropexy and other surgical procedures.

Although the foregoing references have some relevance, they are not suitable for sacral colpopexy, and would not be useful in this latter context. U.S. Pat. No. 6,328,729 (General Surgical Innovations) to Jervis issued Dec. 11, 2001 shows a colporrhaphy method and apparatus in which a tunneling member is advanced and a balloon inflated, thereby dissecting the anatomical space. Again, this device is designed to facilitate dissection of anatomical spaces and is not useful for sacral colpopexy.

United States Patent Application 20060015001 to Staskin et al. (American Medical) issued Jan. 19, 2006 shows a sling delivery system to treat urological disorders. The U-shaped configuration of the sling assembly also allows the sling to be adjusted during and/or after implantation. This device is designed for treatment of incontinence and neither it nor any of the foregoing devices are suitable for performance of sacral colpopexy.

United States Patent Application 20030195386 to Thierfelder et al. (AMS Research Corporation) issued Oct. 16, 2003 shows a surgical kit useful for performing a surgical procedure such as a sacral colpopexy with an implantable Y-shaped suspension for treating pelvic floor disorders such as vaginal vault prolapse. AMS also has a device called the Straight-In™ System which uses a long slender instrument designed for endoscopic use that screws a small coil of wire through the pre-formed Y-graft mesh and into the sacrum, thereby obviating the need to suture the mesh to the anterior longitudinal ligament of the sacrum. This device and the mesh are fairly described in the '386 patent application. Unlike the above-described references, this mesh configuration is created specifically for sacral colpopexy. However, there is no described means of stabilizing the mesh in the desired position during suturing of the mesh to the vagina.

Sacral colpopexy has been performed laparoscopically through multiple ports, in one case three to four ports for a daVinci® robot, and one or two ports for the assistant. The polypropylene mesh was attached robotically to the sacral promontory and to the vaginal apex using Gortex™ sutures. Whether performed manually or robotically, there are still inherent problems with manipulating the end effectors and stabilizing the vagina.

Performing the operation laparoscopically using currently available equipment has several inefficiencies. One of the problematic areas in performing laparoscopic or robotic sacral colpopexy is introduction and positioning of the mesh straps during suturing of the mesh to the vagina. Guiding them into proper orientation is awkward. Maintaining them in the proper position during suturing requires constant vigilance on the part of the assistant as they frequently require repositioning. Additionally, maintaining the mesh straps in position occupies one or more instruments that could be utilized elsewhere (for instance in retracting the surrounding tissues for better visualization). Sometimes portions of the mesh will drape over and obscure the site of interest, particularly during suturing the posterior strap of mesh to the posterior vaginal wall.

It has been proposed in other contexts to stabilize one surgical instrument using a second instrument inserted through another incision. For example, U.S. Pat. No. 7,052,453 to Presthus et al. (Solorant Medical) issued May 30, 2006 shows an incontinence treatment with urethral guide that docks with a probe. Generally, the guide can be inserted into a first body orifice and the probe can be inserted into a second body orifice and placed in a predetermined position relative to the guide so as to position the treatment surface adjacent the target tissue in the second body orifice. The urethral guide and probe may align RF sensors relative to a tissue surface.

It would be greatly advantageous to provide a mesh delivery system that overcomes the alignment and positioning problems using a docking concept as above, rendering the mesh attachment for sacral colpopexy more efficient. If the operation can be rendered more efficient, i.e., less time consuming, and with a lower learning curve, there is potential for the operation to be transformed in to one that is done primarily laparoscopically, similar to what has already occurred with cholecystectomy (removal of the gall bladder).

SUMMARY OF THE INVENTION

It is an object of the present invention to provide a mesh delivery system for sacral colpopexy that facilitates attachment of supporting (anterior and posterior) mesh straps.

It is another object to provide a mesh delivery system for sacral colpopexy (performed via laparotomy or laparoscopically) that uses a conventional grasper/introducer for introducing the mesh in combination with a mesh stabilizer into docked attachment to a vaginal probe which is placed in the vagina exteriorly, to thereby stabilize the inserted mesh for suturing to the vaginal tissue.

It is another object to provide a mesh stabilizer with onboard supply of surgical mesh capable of minimally invasive laparoscopic or robot-assisted laparoscopic introduction into the abdominal cavity.

It is another object to provide a pseudo-elastic mesh stabilizer formed with shape memory alloy and carrying an onboard supply of surgical mesh for compressed-keyhole introduction into the abdominal cavity, and detachment and expansion to a functional state in which it facilitates dispensation of the mesh as well as suturing of the mesh to the anterior and posterior vaginal walls.

It is still another object to provide a pseudo-elastic mesh stabilizer that when surgically inserted into the abdominal body cavity conforms to a vaginal probe inserted into the vagina, docks magnetically to the vaginal apex sandwiching the vaginal apex between itself and the probe, and which carries the onboard supply of surgical mesh anchoring the mesh in position on the vaginal apex and yet allowing repositioning and dispensation of the mesh to the anterior and posterior vaginal walls.

It is another object to stabilize the vagina in a fixed but adjustable position during dissection of the tissue planes necessary to allow safe attachment of mesh to the vagina without causing injury to the rectum or bladder.

It is another object to stabilize the vagina in a fixed but adjustable position during suturing of mesh to the vagina.

It is another object to stabilize the loose end(s) of the surgical mesh (the end(s) not being sutured to the vaginal tissue) to prevent the loose ends from obscuring the surgeons vision during the procedure.

It is another object to allow the surgical mesh to be adjustably positioned with respect to the mesh stabilizer and the vaginal tissue following placement of the mesh stabilizer on the vaginal apex while maintaining stabilization of the mesh by the mesh stabilizer.

Other objects, features, and advantages of the present invention will become more apparent from the following detailed description of the preferred embodiments and certain modifications thereof in which a mesh delivery system is provided for sacral colpopexy. The system generally comprises an elastic mesh stabilizer having a plurality of deployable arms and a magnetic head, a packaging cylinder for introduction of the mesh stabilizer through a conventional port into the abodomen using a conventional grasper or introducer, and a vaginal probe with a magnetic probe tip that interfaces with the mesh stabilizer. The probe may be handheld, robotically-held, or adjustably anchored via a supporting framework to a support surface such as the operating table. The vaginally placed probe essentially acts as a stabilizer for the vaginal tissue during dissection of the bladder and rectum away from the vagina and then during suturing of mesh to the vagina. When the probe is inserted into the vagina to the vaginal apex, the magnetic portion of the mesh stabilizer is attracted to the magnetic tip of the vaginal probe thereby anchoring the mesh stabilizer to the tissue of the vaginal apex inside the abdominal body cavity. The mesh stabilizer is designed to deliver anterior and posterior mesh strap(s) for sacral colpopexy through a standard laparoscopic port, and then stabilize the mesh straps on the vaginal apex during suturing. It is equally beneficial to use the mesh stabilizer via a laparotomy approach. In general use the mesh stabilizer with onboard supply of mesh is, maintained in a compressed configuration while introduced by a standard introducer/grasper through a laparoscopic port into the abdomen. The mesh stabilizer expands to a functional configuration conforming to the interior of the vaginal apex, and magnetically docks to the probe therebeneath. The expansion of the mesh stabilizer deploys and unfurls the onboard mesh from a compressed configuration (unwrinkes the mesh), magnetically docks to the probe head (inserted into the vagina), and positions/anchors the mesh interiorly over the vaginal apex. The docking engagement locks the mesh stabilizer with mesh straps in place in the desired site with the muscular walls of the vagina lying between the vaginal probe and the mesh stabilizer. The endoscopic introducer/grasper is removed, and the now-anchored mesh stabilizer facilitates suturing of the mesh to the anterior and posterior vaginal walls. After permanent suturing, the introducer is reinserted in to the abdomen and used to retrieve the mesh stabilizer component. The system greatly facilitates suturing of the surgical mesh to the vaginal walls and results in a safer, more effective procedure.

BRIEF DESCRIPTION OF DRAWINGS

Other objects, features, and advantages of the present invention will become more apparent from the following detailed description of the preferred embodiments and certain modifications thereof when taken together with the accompanying drawings in which:

FIG. 2 is a side perspective view of a mesh delivery system according to the invention.

FIG. 3 is a front view of the mesh stabilizer 30 while in a flattened (pre-shaped) configuration.

Figure 1:
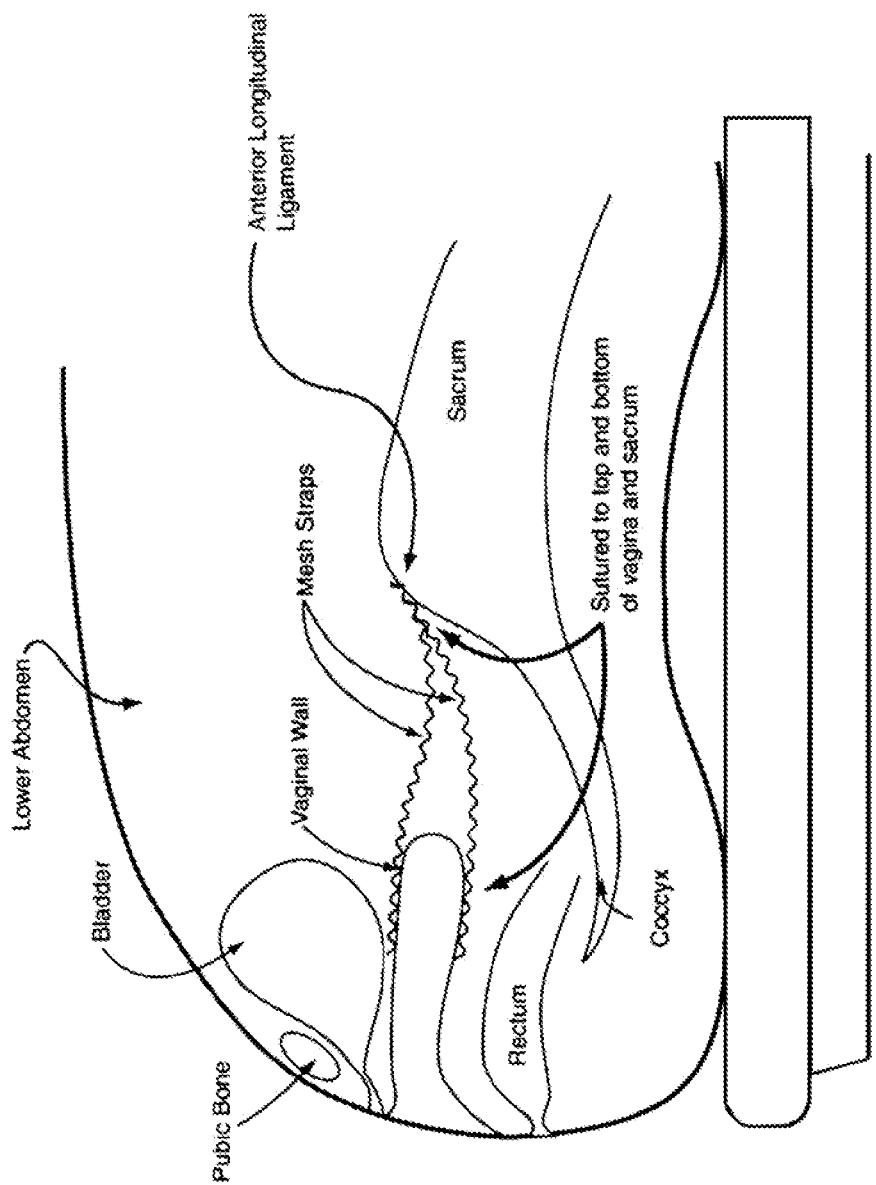
FIG. 1 is a diagrammatic illustration of a completed sacral colpopexy surgery in which straps of mesh attached to the upper vagina inferiorly are suspended on the anterior longitudinal ligament of the sacrum superiorly.
Figure 4:
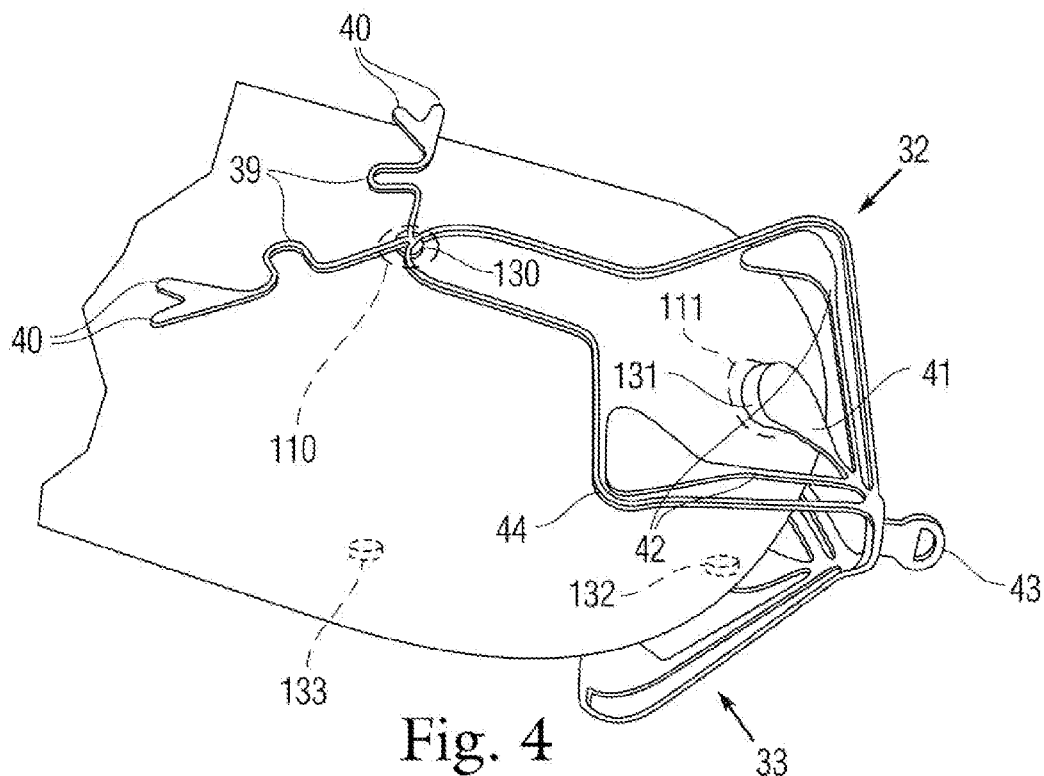
FIG. 4 is a side perspective view of the mesh stabilizer 30 docked to the probe 10 (nosurgical mesh is shown).
Figure 5:
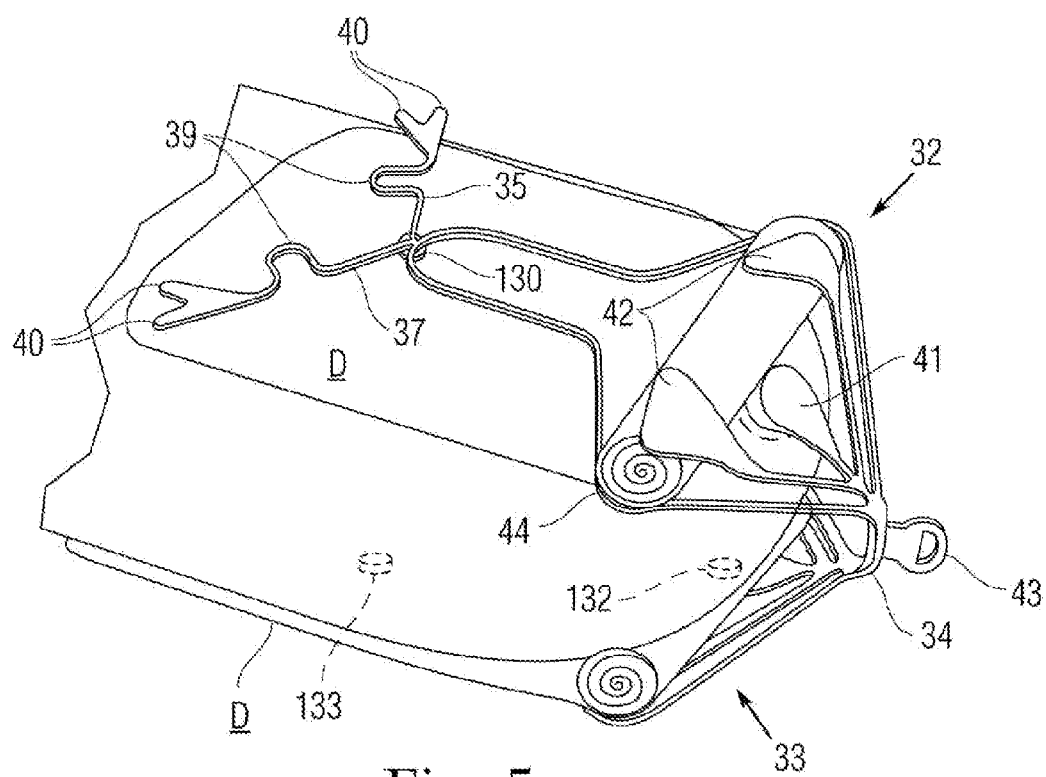
FIG. 5 is a side perspective view of the mesh stabilizer 30 docked to the probe 10 and carrying a payload of mesh (D).

Note that in FIGS. 4-5 an alternate configuration of the loop 39 is an open elbow (mentioned in regard to FIG. 3).

Figure 6:
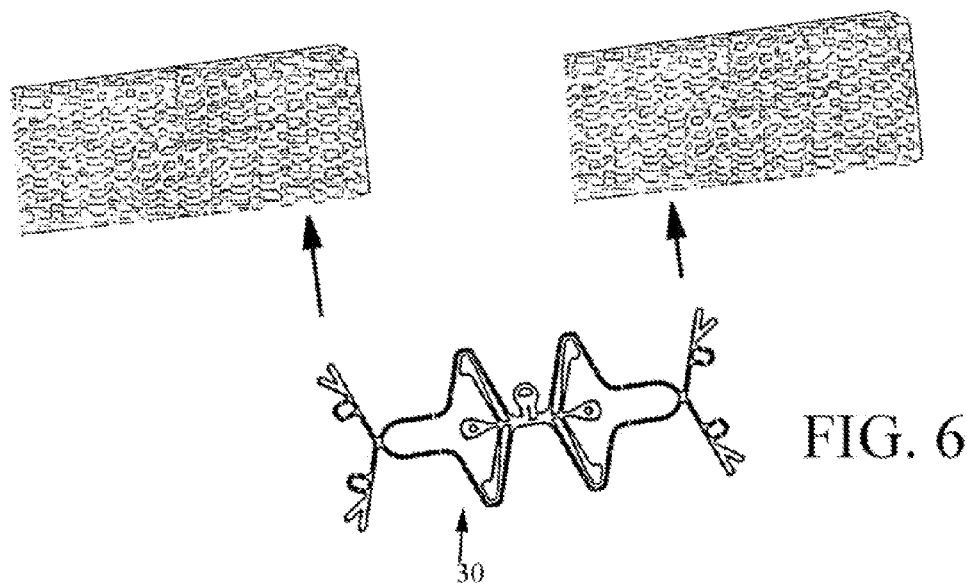

FIG. 6 is a front view of the mesh stabilizer 30 (in the flattened—preshaped configuration) illustrating where the payload of mesh will be loaded.

Figure 7:
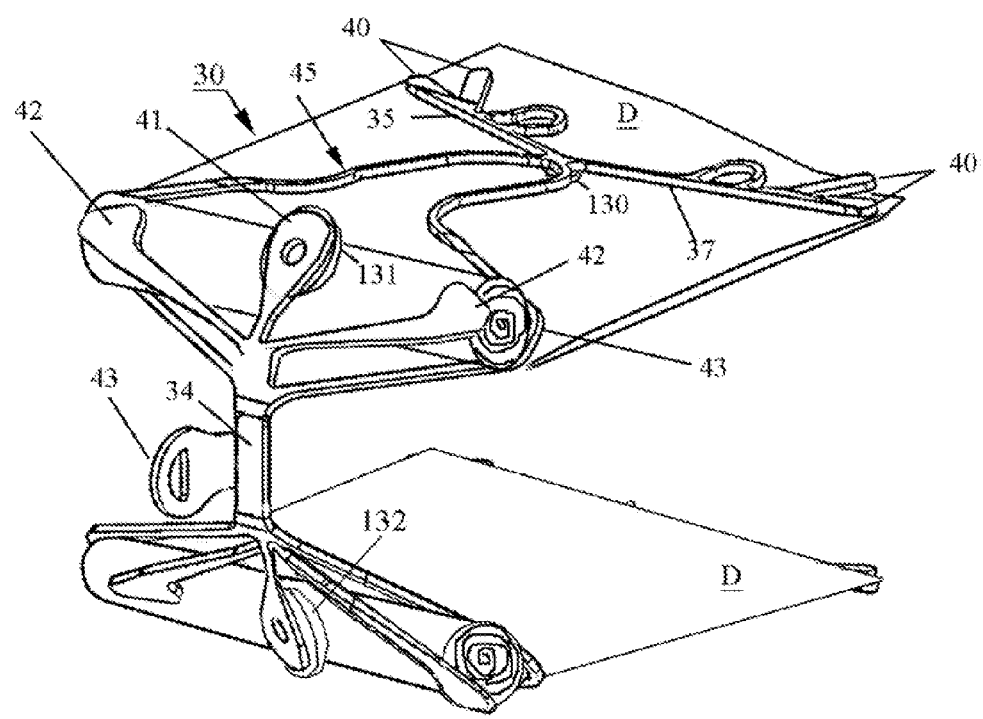

FIG. 7 is a perspective view of the mesh stabilizer 30 with surgical mesh loaded on both sides.

FIG. 8 is a side perspective view of the mesh stabilizer 30 in a compact folded configuration being loaded into the packaging cylinder 137.

FIG. 9 is a side perspective view of the mesh stabilizer 30 inside packaging cylinder 137 being loaded into a surgical port 60 (trocar).

Figure 10:
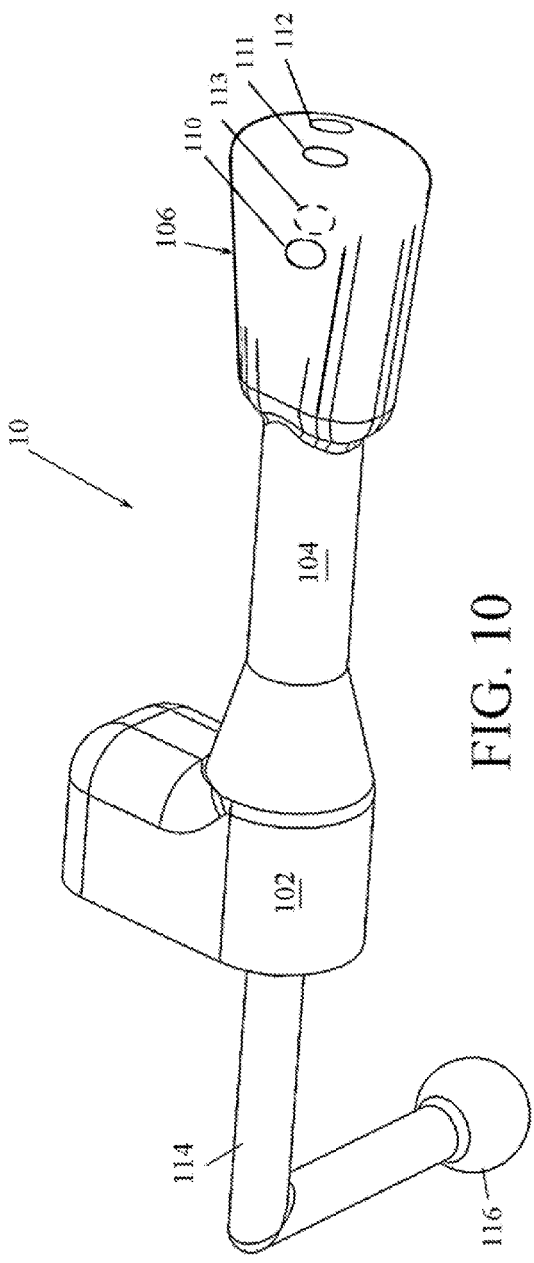

FIG. 10 is a top of the vaginal probe 10.

Figure 11:
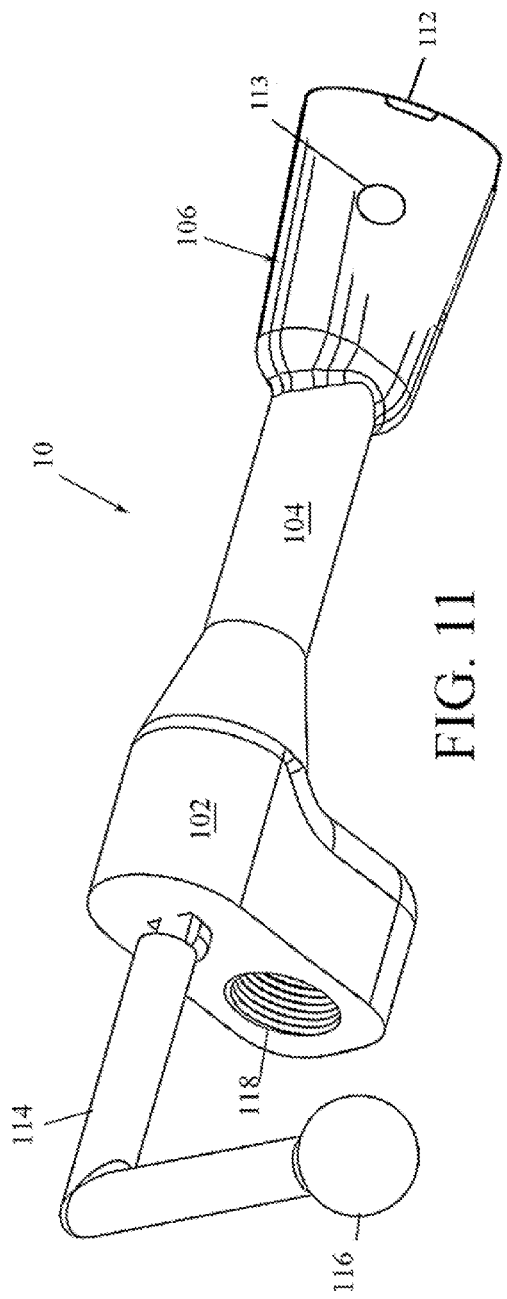

FIG. 11 is a side of the vaginal probe 10.

DETAILED DESCRIPTION OF THE PREFERRED EMBODIMENTS

As described above, the present invention is a method and apparatus for introducing, positioning and anchoring a surgical mesh or implement at a surgical site on an anatomical tissue structure interiorly of the human body. The method and device can be used for all forms of surgical repair of the female condition vaginal prolapse, and is especially well suited for the minimally invasive laparoscopic approach where the surgical mesh is introduced into the female cavity through surgical ports (such a trocars). The present method and device, accurately positions, and reliably stabilizes the surgical mesh against vaginal tissue structure during the surgical procedure. The invention may be used for a variety of different procedure types, such as for delivering surgical mesh, staples or other surgical tools or implements to a site during hernia, cholecystectomy (removal of the gall bladder) or other procedures. A preferred embodiment of the invention will herein be described in the context of a mesh delivery system for sacral colpopexy that is inserted laparoscopically and expands after insertion, and which uses a magnetic docking and holding concept to overcome alignment and positioning problems when placing and securing the surgical mesh on the vaginal tissue.

The invention begins with a vaginal probe having a magnetic probe tip. The probe is inserted into the vagina and is positioned with the probe tip on one side of the vaginal apex, or other anatomical tissue structure for other procedures. A surgical mesh assembly is loaded (while in a compressed state) into a cylinder, the cylinder is loaded into a trocar or other port, and the surgical mesh assembly is then dispensed from the cylinder through the port into the abdomen using a conventional grasper or needle driver. Once the mesh assembly passes through the port (inside the abdomen) the mesh assembly expands from its compressed state to an expanded state, and it is maneuvered inside the abdominal cavity by a pair of graspers, needle driver or other instrument, into position at a desired surgical site against the tissue of the vaginal apex. The mesh assembly has at least one magnet attached and, once in position, the magnet is attracted to the magnetic probe head positioned directly behind and inside the vaginal apex. This magnetically couples the mesh assembly at the surgical site to the anatomical tissue structure. The mesh assembly has a payload of mesh attached to it, and when it is placed at the surgical site, it allows the of the mesh on the vaginal tissue to be adjusted while still keeping it tensioned and flat against the tissue of the vaginal apex during permanent suturting. When suturing is completed the mesh stabilizer portion of the mesh assembly is grasped and removed. This process of placing, holding and suturing the surgical mesh to the vaginal apex is less time consuming, less prone to error than conventional surgical processes, and may facilitate transition to single-incision laparoscopic or robotic approaches to sacrocolpopexy.

FIG. 2 illustrates the mesh stabilizer 30 as it docks and conforms to probe 10, clamping the tissue of the vaginal apex (not shown) there between. The probe 10 may be any conventional vaginal probe modified as described below, and may be handheld, robotically-held, or adjustably held via a supporting framework to a support surface such as the operating table. In accordance with the present invention, the probe 10 is equipped with at least one permanent magnetic disk 110 embedded in its tip, and preferably a plurality (such as four) permanent magnetic disks 110-113. In use, the vaginally placed probe 10 is inserted into the vagina and essentially acts as a stabilizer for the vaginal tissue during dissection of the bladder and rectum away from the vagina and then during suturing of mesh to the vagina.

The mesh stabilizer 30 is a bent wire frame structure likewise having at least one permanent magnetic disk 130 secured thereto, and preferably a plurality (four) permanent magnetic disks 130-133 cooperating with those of probe 10. In the illustrated embodiment, the magnetic disks of probe 10 and those of mesh stabilizer 30 align in pairs 110:130; 111:131; 112:132; 113:133, which allows for indexed relative linear and rotational positioning. When the probe 10 is inserted into the vagina to the vaginal apex, the magnet(s) 130-133 of the mesh stabilizer 30 are attracted to the magnets 110-113 of the probe tip thereby anchoring the mesh stabilizer 30 to the vaginal apex inside the abdominal body cavity.

The mesh stabilizer 30 may be formed by laser-cutting sheet stock into a flat wire frame structure (as shown in FIG. 3) and then bending the flat structure into a three-dimensional shape (as shown in FIG. 2) conforming to the probe 10 head.

FIG. 3 is a front view of the mesh stabilizer 30 cut pattern prior to bending or attachment of permanent magnetic disks 130-133. Mesh stabilizer 30 may be laser cut from any resilient or pseudoeleastic sheet material in which deformation can be fully recovered upon unloading to the zero-stress state. Many metals exhibit pseudoelastic effects, but in the present context Ni—Ti based alloys (as well as other shape memory alloys) are preferred because of their material properties (super elastic) as well as their chemical and biological compatibility with the human body. See, Castleman et al., "The Biocompatibility of Nitinol," in Biocompatibility of Clinical Implant Materials, vol. 1, Williams D F (ed), CRC Press, p 129 (1981). The pseudoelastic alloy of the present invention preferably contains 55-56 percent Nickel and 44-45 percent Titanium, plus a remainder of one or more additional ternary alloying elements. A simple binary Ni—Ti of 56% Nickel and 44% Titanium is well suited and readily available from a variety of vendors including Norman Noble, a leading medical supplier. The mesh stabilizer 30 further comprises a first side 32 and a second side 33 joined together at a juncture 34, said first side and second side 32, 33 comprising diametrically-extending mesh stabilizing wire frameworks. A small looped tab 43 protrudes from the junction 34. In the preferred embodiment the mesh stabilizing wire frameworks on the first side and second side 32, 33 are mirror opposites. Each mesh stabilizing framework further comprises a closed-loop portion 45 and a pair of outwardly-protruding spring arms 35, 37 diverging outward from a distal end of the closed loop portion 45. The protruding spring arms 35, 37 are formed with a loop 39, or elbow or the like approximately midlength for seating the jaws of a grasping instrument. This allows the spring arms 35, 37 to be gripped and open or closed. The protruding spring arms 35, 37 are also formed with a plurality of distal fingers 40 for catching the weaves of the mesh and spreading/tensioning it across the vaginal apex. The closed-loop portion 45 of each mesh stabilizing framework is widened toward the juncture 34 to provide a guide slot 44 for dispensing mesh, and so the guide slot 44 is slightly wider than the mesh to be dispensed. The strips of mesh are caught in the fingers 40 and threaded under the mesh stabilizing framework up through the widened guide slot 44.

A head 41 and opposing arms 42 branch into the open space of each guide slot 44. The two heads 41 serve as a mounting post for two of the centering magnets 131, 132 of FIG. 2. The juncture of each closed-loop portion 45 with spring arms 35, 37 serve as the mounting point for the other two centering magnets 130, 133 of FIG. 2.

The opposing arms 42 are carrier arms for securing the onboard payload of mesh. Specifically, when the strips of mesh are threaded under the mesh stabilizing framework up through guide slots 44, the excess length of mesh is folded or rolled up and tucked under the carrier arms 42. The carrier arms 42 are elongate and resilient, with hands at the end to impose a bias onto both sides of each roll of mesh. The bias is sufficient to keep the roll or folds intact and yet allow adjustment of the position of the mesh relative to the mesh stabilizer and vaginal apex while maintaining stabilization of the mesh on the mesh stabilizer.

After initial laser-cutting as described above, the mesh stabilizer 30 is permanently formed by bending into a three-dimensional shape with the first side 32 and a second side 33 bent at an angle at juncture 34 in order to generally conform to the arc of the probe 10 head. This way, as seen in FIG. 4, the mesh stabilizer 30 attaches to the probe 10 head with the first side 32 overttop and second side 33 underneath. The four disc permanent magnets 130-133 are attached as shown in FIG. 2, and the small looped tab 43 is bent at a right angle to protrude rearward from the junction 34. This provides a stem for grasping and ease of insertion/removal. During insertion the magnets 130-133 of mesh stabilizer 30 grip the corresponding magnets 110-113 embedded in the probe head and secure the mesh stabilizer 30 in place. The opposing resilient spring arms 35, 37 and fingers 40 of mesh stabilizer 30 grip the vaginal tissue over the face of the probe head by both overtop and underneath, and at this point the inserter/grasper can be released from the tab 43 and withdrawn.

In general use the mesh stabilizer 30 is preloaded with a payload supply of mesh (D), which mesh (D) is folded and maintained in a compressed configuration during introduction by a standard grasper, needle driver through a laparoscopic port (such as a trocar) into the abdomen. As seen in FIG. 5, each mesh stabilizer 30 is adapted for caning a payload of two strips of mesh (D), one for the upper vaginal apex and one for the lower. Alternatively, the mesh stabilizer 30 will accommodate a Y-shaped single piece of surgical mesh.

FIG. 6-7 illustrates the process of inserting a payload of mesh (D) into the mesh stabilizer 30. The distal fingers 40 of the spring arms 35, 37 are engaged to the strip of the mesh (D) at the corners at one end, and the other end of the mesh (D) is inserted up through the closed-loop portion 45 of the stabilizing framework through slot 43. The inserted end is then rolled or folded up and is tucked beneath the carry arms 42, as seen in FIG. 7.

FIG. 8-9 illustrates the packaging cylinder 137 which facilitates the placement of the mesh stabilizer 30 into a surgical port (such as a trocar) in preparation for introducing the mesh stabilizer 30 into a body cavity along with its payload of mesh (D). The spring arms 40 of mesh stabilizer 30 are folded together (collapsed) with the preloaded mesh strips (D) by squeezing the mesh stabilizer 30 with preloaded mesh (D) laterally while simultaneously pulling the mesh stabilizer 30 and mesh (D) into the packaging cylinder 137. In this manner, the mesh stabilizer 30 is fully and slidably preloaded into the packaging cylinder 137, and is capped with a collar 134, sterilized and packaged for later use. The collar 134 is essentially a cap with a central perforation which remains sealed around the protruding grasping tab 43 on the mesh stabilizer 30 to maintain insufflation when the tubular cylinder 137 is advanced into the laparoscopic trocar 60, yet still allowing passage of a laparoscopic grasper or needle driver through the collar 134 to advance the mesh stabilizer 30 into the abdomen. The collar 34 maintains insufflation by sealing around the laparoscopic instrument. The collar 134 is similar to other diaphragm valves as typically used in laparoscopic based procedures for allowing laproscopic access yet preventing the release of insufflation gases. When it is desirable to use the mesh stabilizer 30, the packaging cylinder 137 is unpackaged, and loaded into a conventional trocar 60 or other port, and the mesh stabilizer 30 is inserted through the port 60 into the abdomen by pushing with a conventional grasper or needle driver. The natural expansion of the mesh stabilizer 30 deploys and unfurls the onboard mesh from a compressed configuration (unwrinkes the mesh).

The packaging cylinder 137 is a tubular member with rubber collar 134 mounted at one end. The cylinder 137 is adapted for insertion through a standard trocar or port 60 to provide a passage into the body cavity. Collar 134 is an elastomeric member that functions as a gas valve so it can work in conjunction with the trocar or similar surgical port. With the mesh stabilizer 30 rolled inside cylinder 137 in its compressed configuration, a surgeon can easily introduce the stabilizer 30 into the body cavity using standard graspers or needle drivers. Since the mesh stabilizer 30 is rolled, the grasping tab 43 remains fully accessible at the very center and is accessible by the graspers/needle drivers. Mesh stabilizer 30 is then pushed out of the cylinder 137 and it expands to the configuration shown in FIG. 7 (but with mesh on both sides of the mesh stabilizer), and can be docked to the vaginal probe 10, which precisely positions/anchors the mesh stabilizer 30 to the tissue of the vaginal apex inside the abdominal body cavity. The docking engagement holds the mesh stabilizer 30 with mesh straps in place in the desired site with the muscular walls of the vagina lying between the vaginal probe and the mesh stabilizer but still allows the surgeon to adjust the position of the mesh relative to the vaginal apex and mesh stabilizer while still maintaining stabilization of the mesh on the vaginal apex. The grasper/needle driver is then removed, and the now-anchored mesh stabilizer 30 facilitates suturing of the mesh to the anterior and posterior vaginal walls. After permanent suturing, the grasper/needle driver is reinserted into the abdomen and used to retrieve the mesh stabilizer 30. The system greatly facilitates suturing of the surgical mesh to the vaginal walls and results in a safer, more effective procedure, and may facilitate transition to single-incision laparoscopic or robotic approaches to sacrocolpopexy.

The present invention is suited for use with any surgical table, and both components 10, 30 may be manually, mechanically or robotically manipulated. The vaginal probe 10 may be distally mounted on a flexible/locking stabilizing arm of a surgical table that thereby securely holds the probe 10 during the sacral colpopexy procedure (which indeed requires a stable probe during suturing of mesh to the vagina), or a manually supported probe. In practice, the mesh stabilizer 30 may be packaged as a pre-loaded (or semi-preloaded) sub-assembly inside cylinder 137 as shown in FIG. 9, or may be loaded in the cylinder by the surgeon just prior to the surgical procedure.

When the mesh stabilizer 30 is deployed into the abdomen area, the opposing spring arms 35, 37 and opposing foldable mesh (D) unfurls to its open position (shown in FIG. 7). The probe 10 is inserted into a fixed opposing position within the vagina, and the mesh stabilizer 30 embraces and docks with the probe 10, collapsing around the front and back walls of the vaginal cavity. When the mesh stabilizer 30 is fully docked with the probe 10 it sandwiches both the mesh and vaginal muscularis there between so that one strap of mesh (D) sits opposed to the front vaginal wall and the other strap to the back vaginal wall. This securely positions the mesh on the vaginal walls to which it will be sutured, and adds some frictional resistance to withdrawal of the mesh through the closed-loop portion of the mesh stabilizer 30 stabilizing framework, thereby allowing the surgeon to adjust the position of the mesh relative to the vaginal apex and mesh stabilizer while still maintaining stabilization of the mesh on the vaginal apex.

Virtually any vaginal probe 10 may be used for present purposes (including vaginal probes without magnets but improve stabilization of the mesh stabilizer on the vaginal apex the magnetic attachment is recommended). FIGS. 10 and 11 are top and bottom side perspective views, respectively, of an exemplary vaginal probe 10. Probe 10 generally comprises a body 102 leading to a shaft 104 for insertion in the vagina, and a probe head 106 distal on the shaft 104. The probe head 106 is slightly flattened, with a generally trapezoidal horizontal and vertical cross-section flaring outward from the shaft 104, with rounded corners and edges so that it is more anatomically shaped to better conform the natural shape of the vagina than conventional vaginal probes. The probe head 106 may be tapered rearwardly of the tip to prevent inadvertent pop-off of the mesh stabilizer 30. Exemplary dimensions are 7 cm×5 cm×2.5 cm×4 cm, resulting in a 5 cm×2.5 cm probe end. The thicker tip can help prevent the spring arms 35, 37 of the stabilizer 30 from coming off (especially if the embodiment relies strictly on clamping).

In summary, the operating sequence of the mesh stabilizer 30, packaging cylinder 137 and vaginal probe 10 generally includes six discrete steps: 1) introduction; 2) opening; 3) coupling; 4) detachment; 5) suturing, and 6) removal.

At 1) introduction, the mesh stabilizer 30 is loaded with mesh (D) and rolled/pulled inside the packaging cylinder 137. In this state, the spring arms 35, 37 are constrained in a closed state for introduction through the surgical port (60) and into the abdomen. The preloaded packaging cylinder 137 is then placed in the surgical port 60 (FIG. 9).

At 2) opening, the cylinder 137 and mesh stabilizer 30 are pushed into the abdomen with the grasper/needle driver, extending into abdominal region. Once in the abdomen, the stabilizer 30 is exposed (freed from cylinder 137), and spring arms 35, 37 of the mesh stabilizer 30 open to a deployed position as shown in FIG. 7.

At step 3) coupling, the open spring arms 35, 37 are advanced over the vaginal apex and probe 10 head to begin the magnetic docking between the mesh stabilizer 30 and the vaginal probe head magnets. The probe head remains stationery.

At 4) detachment, the grasper/needle driver is removed leaving the stabilizer 30 attached to the probe 10.

At 5) suturing, the surgeon has an unobstructed view of the vaginal muscularis because the excess mesh straps are being contrained by the mesh stabilizer and not hanging down and obscuring the surgeons vision, which facilitates the suturing of the mesh straps to the vaginal muscularis.

Upon completion of suturing, the grasper/needle driver can be reinserted and reattached to the stabilizer 30.

At 6) the mesh stabiler is removed from the abdomen back through the surgical port 60.

One skilled in the art should readily understand that there may be other mechanical mechanisms to achieve the requisite docking between the probe head 106 and mesh stabilizer 30, and the illustrated mechanisms are exemplary. In addition to the basic functionality described above, the probe 10 may be modified as desired to improve suitability to the task. For example, there may be one probe design for use with a flush vaginal vault, and one for use with a retained cervix. Alternatively, the vaginal probe 10 may be provided with a plurality of detachable tips for accomodating different vaginal configurations including the retained cervix. The vaginal vault probe may be equipped with a grasping mechanism at its tip to further stabilize the vagina and further minimize the risk of inadvertent pop-off of the mesh stabilizer 30 from the vaginal apex. The locking mechanism may be paired built-in grasping forceps, paired conical tips that prevent slippage without grasping, or paired suction channels to prevent slippage by creating a vacuum between the probe and the vaginal muscularis. A retained cervix vaginal probe must accommodate the cervix at its anterior tip. This may entail a shorter probe component that would sit within the endocervix to stabilize the cervix. Again, the probe 10 may contain some form of grasping component as described above to further stabilize the cervix and pull it flush against the probe.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

What is claimed is:

1. A mesh stabilizer for stabilizing and dispensing a supply of surgical mesh during a sacral colpopexy procedure, comprising a resilient body, said body further comprising a first mesh stabilizing framework and a diametric second mesh stabilizing framework integrally joined to said first mesh stabilizing framework at a junction, said first mesh stabilizing framework comprising a thin flexible structure extending away from said junction to a first head and a first magnet affixed to said first head, said second mesh stabilizing framework being identical to said first mesh stabilizing framework and extending diametrical therefrom to a second head, and having a second magnet affixed to said second head, and a pair of long, slender spring arms integrally attached to said body and protruding outward therefrom away from said junction, for tensioning and removably anchoring a strip of surgical mesh there beneath.

2. The mesh stabilizer according to claim 1, wherein said resilient body is comprised of a unitary piece of shape memory material.

3. The mesh stabilizer according to claim 2, wherein said resilient body is cut from a sheet of shape memory material and formed into a three-dimensional structure.

4. The mesh stabilizer according to claim 1, wherein said first pair and second pair of protruding spring arms each comprise a plurality of distally-forked fingers for catching strands of said mesh.

5. The mesh stabilizer according to claim 1, wherein said first magnet affixed to said first head and said second magnet affixed to said second head are both permanent magnetic disks.

6. The mesh stabilizer according to claim 5, further comprising a plurality of magnets attached to said first head and a plurality of magnets attached to said second head.

7. The mesh stabilizer according to claim 5, further comprising a third magnet attached to said juncture.

8. The mesh stabilizer according to claim 1, further comprising a pair of carrier arms attached to each of said first and second mesh stabilizing frameworks for securing a supply of mesh thereto.

9. The mesh stabilizer according to claim 8, wherein said carrier arms allow withdrawal of said mesh from said said first and second mesh stabilizing frameworks but impart frictional resistance against withdrawal of the mesh, thereby maintaining stability of the mesh on the vaginal apex.

10. A surgical mesh delivery system comprising:
a mesh stabilizer for securing and positioning surgical mesh, said mesh stabilizer comprising a wireframe resilient body formed with a first mesh stabilizing framework and a second mesh stabilizing framework integrally joined to said first mesh stabilizing framework at a junction, said first mesh stabilizing framework comprising a thin flexible structure extending away from said junction to a first head and a first magnet affixed to said first head, said second mesh stabilizing framework being identical to said first mesh stabilizing framework and extending diametrical therefrom to a second head, a second magnet affixed to said second head, and a pair of outwardly-protruding spring arms for tensioning and anchoring a strip of surgical mesh there beneath;
a vaginal probe configured for docking engagement with said mesh stabilizer via said first magnet and said second magnet; and
a packaging cylinder for containing and for introduction of said mesh stabilizer into a body cavity through a surgical port while in a compressed configuration.

11. The surgical mesh delivery system according to claim 10 wherein each of said pair of spring arms is formed with a bend for seating with grasper jaws or needle drivers.

12. The surgical mesh delivery system according to claim 10, wherein said mesh stabilizer comprises at least one carrier arm for carrying a strip of surgical mesh.

13. The surgical mesh delivery system according to claim 12 wherein said mesh stabilizer comprises a pair of carrier arms each attached to a respective opposing mesh stabilizing framework for carrying a strip of surgical mesh on each framework.

14. The surgical mesh delivery system according to claim 13, wherein each said spring arm further comprises a plurality of distal tines for engaging said strip of surgical mesh.

15. The surgical mesh delivery system according to claim 10, wherein said spring arms prevent said strip of surgical mesh from obstructing a surgeon's line of view.

16. The surgical mesh delivery system according to claim 10, wherein said mesh is adjustable relative to said mesh stabilizer and vaginal apex while maintaining stabilization of the mesh on the mesh stabilizer.

17. The surgical mesh delivery system according to claim 10, wherein said mesh is adjustable relative to the mesh stabilizer and vaginal apex.

18. The surgical mesh delivery system according to claim 10, wherein said vaginal probe comprises a removable probe tip.

19. The surgical mesh delivery system according to claim 14, wherein each said spring arm is composed of a shape memory alloy comprising a pseudoelastic alloy of Nickel and Titanium.

20. The surgical mesh delivery system according to claim 10, wherein said vaginal probe comprises a plurality of detachable tips for accomodating different vaginal configurations including a retained cervix.

21. A mesh stabilizer for stabilizing a supply of surgical mesh, comprising:
a resilient body formed with a first mesh stabilizing framework extending outward from a junction, and a second mesh stabilizing framework extending outward from said junction diametric to said first mesh stabilizing framework, each of said first and second mesh stabilizing frameworks having a mesh carrier positioned part way along its length for securing an onboard payload of mesh; and
a plurality of magnets, one attached to each of said first and second mesh stabilizing frameworks outwardly of the mesh carriers on said first and second mesh stabilizing frameworks.

22. The mesh stabilizer according to claim 21, further comprising an additional magnet attached to said junction.

* * * * *